(12) United States Patent
Lux (10) Patent No.: US 12,029,570 B1
(45) Date of Patent: Jul. 9, 2024

(54) METHOD AND SYSTEM FOR MEASURING UNIPOLAR AND BIPOLAR CARDIAC ELECTROGRAM FRACTIONATION

(71) Applicant: Neucures Inc., Los Angeles, CA (US)

(72) Inventor: Robert L. Lux, Park City, UT (US)

(73) Assignee: NEUTRACE INC., Longwood, FL (US)

( * ) Notice: Subject to any disclaimer, the term of this patent is extended or adjusted under 35 U.S.C. 154(b) by 73 days.

(21) Appl. No.: 17/073,220

(22) Filed: Oct. 16, 2020

(51) Int. Cl.
*A61B 5/00* (2006.01)
*A61B 5/366* (2021.01)
*A61B 5/30* (2021.01)
*A61B 5/339* (2021.01)

(52) U.S. Cl.
CPC .............. *A61B 5/366* (2021.01); *A61B 5/30* (2021.01); *A61B 5/339* (2021.01)

(58) Field of Classification Search
None
See application file for complete search history.

(56) References Cited

U.S. PATENT DOCUMENTS

| | | | | |
|---|---|---|---|---|
| 7,676,264 | B1 * | 3/2010 | Pillai | A61B 5/349 607/9 |
| 8,676,305 | B2 * | 3/2014 | Hayam | A61B 5/361 607/9 |
| 8,712,519 | B1 * | 4/2014 | Panescu | A61N 1/3684 607/18 |
| 9,278,220 | B2 * | 3/2016 | Ghosh | A61B 5/282 |
| 9,282,907 | B2 * | 3/2016 | Ghosh | A61B 5/318 |
| 10,398,331 | B2 * | 9/2019 | Relan | G16H 50/20 |
| 11,229,393 | B2 * | 1/2022 | Relan | A61B 5/366 |
| 11,439,339 | B1 * | 9/2022 | Lux | A61B 5/367 |
| 2007/0197929 | A1 * | 8/2007 | Porath | A61B 5/349 600/509 |
| 2007/0208260 | A1 * | 9/2007 | Afonso | A61B 5/287 600/300 |
| 2009/0192393 | A1 * | 7/2009 | Hayam | A61B 5/283 600/509 |
| 2015/0032016 | A1 * | 1/2015 | Ghosh | A61B 5/349 600/517 |
| 2015/0032171 | A1 * | 1/2015 | Ghosh | A61B 5/287 607/18 |
| 2017/0156612 | A1 * | 6/2017 | Relan | A61B 5/364 |
| 2020/0046238 | A1 * | 2/2020 | Relan | G16H 50/20 |

* cited by examiner

*Primary Examiner* — Shirley X Jian (74) *Attorney, Agent, or Firm* — Caldwell Intellectual Property Law (57) ABSTRACT

A method for quantifying a metric indicative of a condition of cardiac tissue in an electrogram is disclosed. The method comprises detecting extrema in the electrogram, analyzing the detected extrema, selecting certain extrema based on a threshold and generating a fractionation metric comprising a count of the selected extrema.

15 Claims, 10 Drawing Sheets

FIG. 9

METHOD AND SYSTEM FOR MEASURING UNIPOLAR AND BIPOLAR CARDIAC ELECTROGRAM FRACTIONATION

FIELD

Embodiments of the present invention relate to systems and methods for use in quantitating and characterizing a plurality of signals from the heart.

BACKGROUND

Electrical activity generated by the heart can be measured by arrays of electrodes placed on and within the cardiac muscle. The recorded tracings are called electrograms (EGMs). The dominant wave of EGMS, the depolarization wave (QRS), reflects the electrical depolarization (excitation) of the heart that leads to its mechanical contraction that pumps blood.

The depolarization wave of each EGM contains information about the health of the tissue near the electrode and quantitative measurements of the wave provides a means to separate normal and abnormal cardiac tissue. Aspects of the depolarization wave relate specifically to the heart tissue local to the electrodes.

SUMMARY

This Summary is provided to comply with 37 C.F.R. § 1.73, requiring a summary of the invention briefly indicating the nature and substance of the invention. It is submitted with the understanding that it will not be used to interpret or limit the scope or meaning of the claims.

There is a requirement to measure features of the EGM depolarization wave such as time of passage of the wave (local activation time or LAT), voltage amplitude, and fractionation.

Broadly, embodiments of the invention disclose a system and a method to determine a metric indicative of fractionation within each electrogram. Fractionation refers to the non-smooth, jagged features of an EGM that reflect abnormal tissue. The technique includes the following steps:

- determining a Local Activation Time (LAT) of the EGM depolarization wave from its first derivative with respect to time—at the time of the minimum dV/dt;
- determining a second derivative with respect to time of the depolarization wave of each EGM, $d^2V/dt^2$;
- measuring a minimum maximum (mini-max) noise in a time interval of the EGM when there is no fractionation, e.g. in any 30-millisecond interval in the 300 milliseconds prior to the LAT;
- delineating the beginning and end of the EGM depolarization wave, $QRS_{onset}$ and $QRS_{end}$ surrounding the LAT using a noise threshold;
- detecting all extrema (peaks and nadirs) of $d^2V/dt^2$ in both the 30-millisecond interval preceding the QRS and the $QRS_{onset}$ to $QRS_{end}$ interval;
- determining the magnitudes of the excursions between adjacent extrema for both intervals; and.
- Counting a number of excursions greater than the maximum excursion in the 30-millisecond noise interval, that is $EGM_{FRAC}$=number of significant excursions.

Other aspects of the invention, will be apparent from the written description below.

DETAILED DESCRIPTION

In the following description, for purposes of explanation, numerous specific details are set forth in order to provide a thorough understanding of the invention.

Reference in this specification to "one embodiment" or "an embodiment" means that a particular feature, structure, or characteristic described in connection with the embodiment is included in at least one embodiment of the invention. The appearances of the phrase "in one embodiment" in various places in the specification are not necessarily all referring to the same embodiment, nor are separate or alternative embodiments mutually exclusive of other embodiments. Moreover, various features are described which may be exhibited by some embodiments and not by others. Similarly, various requirements are described which may be requirements for some embodiments but not others.

Moreover, although the following description contains many specifics for the purposes of illustration, anyone skilled in the art will appreciate that many variations and/or alterations to said details are within the scope of the present invention. Similarly, although many of the features of the present invention are described in terms of each other, or in conjunction with each other, one skilled in the art will appreciate that many of these features can be provided independently of other features. Accordingly, this description of the invention is set forth without any loss of generality to, and without imposing limitations upon, the invention.

As will be appreciated by one skilled in the art, the aspects of the present invention may be embodied as a system, method, or computer program product. Accordingly, aspects of the present invention may take the form of an entirely hardware embodiment, an entirely software embodiment (including firmware, resident software, micro-code, etc.), or an embodiment combining software and hardware aspects that may all generally be referred to herein as a "circuit," "module," or "system." Furthermore, aspects of the present invention may take the form of a computer program product embodied in one or more computer readable medium(s) having computer readable program code embodied thereon.

Figure 1:
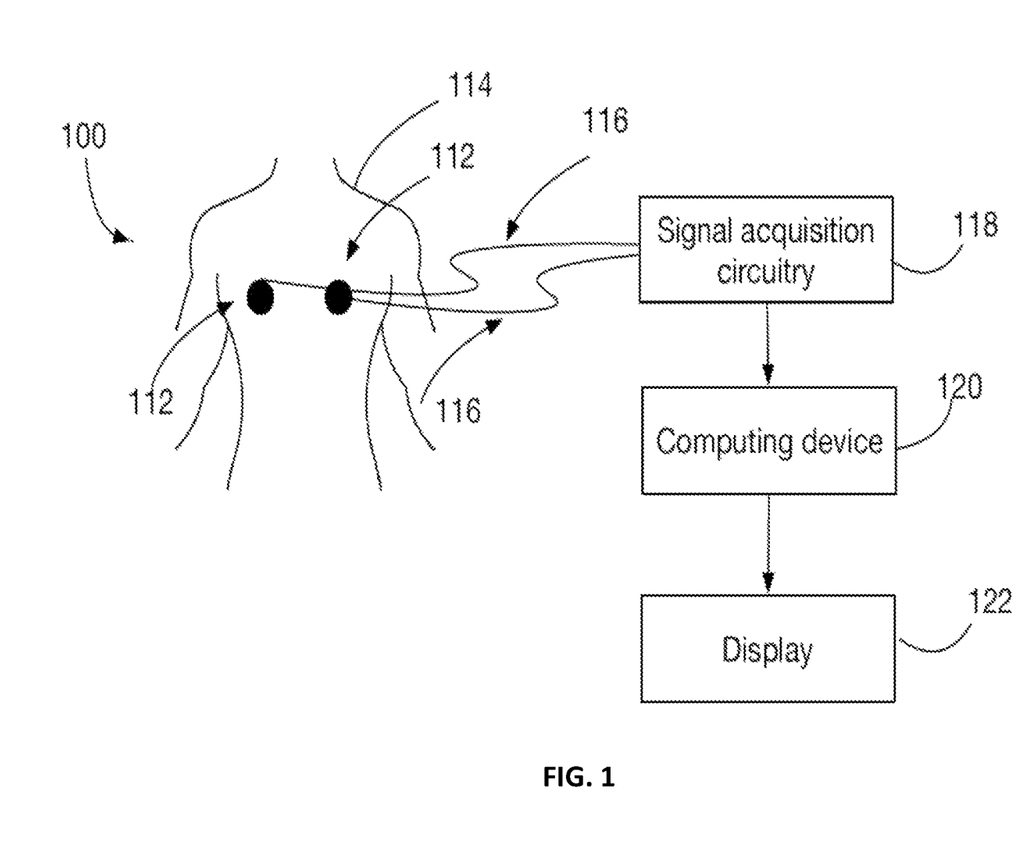
FIG. 1 shows an exemplary system for extracting QRS features from EGMs, in accordance with one embodiment of the invention.

FIG. 1 illustrates an exemplary system 100 for acquiring EGM signals in accordance with one embodiment of the invention. As will be seen, the system 100 comprises a plurality of electrodes 112 that that may be positioned on the torso of a patient 114. The electrodes 112 may be configured to measure the body-surface potentials (electrocardiograms or ECGs) of the patient 114, e.g. the torso-surface potentials of a patient 114. Additional electrodes on catheters inserted into the heart cavity or on the heart surfaces collect signals called electrograms (EGMs) Each electrode signal (body surface or heart) is coupled via an electrical lead 116 to an interface/amplifier circuitry 118.

The interface/amplifier circuitry 118 may be configured to amplify the signals from the electrodes 112 and provide the signals to a computing device 120. In other embodiments, a wireless connection may be used to transmit the signals sensed by electrodes 112 to the interface/amplifier circuitry 118 and, in turn, the computing device 120, e.g., as channels of data. For example, the interface/amplifier circuitry 118 may be electrically coupled to each of the computing device 120 using, e.g., analog electrical connections, digital electrical connections, wireless connections, bus-based connections, network-based connections, internet-based connections, etc. The computing device 120 may be operatively coupled to a display device 122 for displaying information to an operator.

The device 120 may record and analyze the torso-surface potential signals sensed by the electrodes 112 and amplified/conditioned by the interface/amplifier circuitry 118. The computing device 120 may include one or more processors which may be configured to analyze the signals received from the electrodes 112 to provide an electrical activation information or data such as cardiac electrical activation times, e.g., representatives of an actual, or a local, electrical activation times of one or more regions of the patient's heart as will be further described herein.

Additionally, the computing device 120 may be configured to provide graphical user interfaces 126 depicting the electrical activation times obtained using the electrodes 112 on a display device 122.

The computing device 120 may be coupled to a memory 124 by a suitable data bus.

The computing device 120 may optionally remove noise from the signals captured from the electrodes 112.

Various techniques may be employed to remove noise detected in the signals. For example, power line or random noise filters may be applied to all EGM signals recorded.

Once EGM signals with acceptable noise levels are obtained from the electrodes 112, the processing in the computing device 120 may proceed to calculating a first derivative and a second derivative of the N EGM signals.

The computing device 120 may also detect a depolarization wave in the EGM signals and separates a window of the signal around the time when an absolute value of the first derivative with respect to time (dv/dt) of the signal is at a maximum.

The techniques disclosed herein may be used with systems that include graphical user interfaces for use by users to evaluate a patient's cardiac health and/or adjust cardiac therapy. As described herein with reference to FIG. 1, the exemplary systems and methods described herein may use display apparatus 122 including a graphical user interface. The graphical user interface may be configured to, among other things, present information for use in assisting a user in evaluating a patient's cardiac health. For example, the graphical user interface may be configured to display heart's depolarization time information and other metrics referenced to $QRS_{onset}$. Further, for example, the graphical user interface may be configured to display a spatial map of the electrical activation times based on a geometric location of the electrodes relative to each other.

Figure 2:
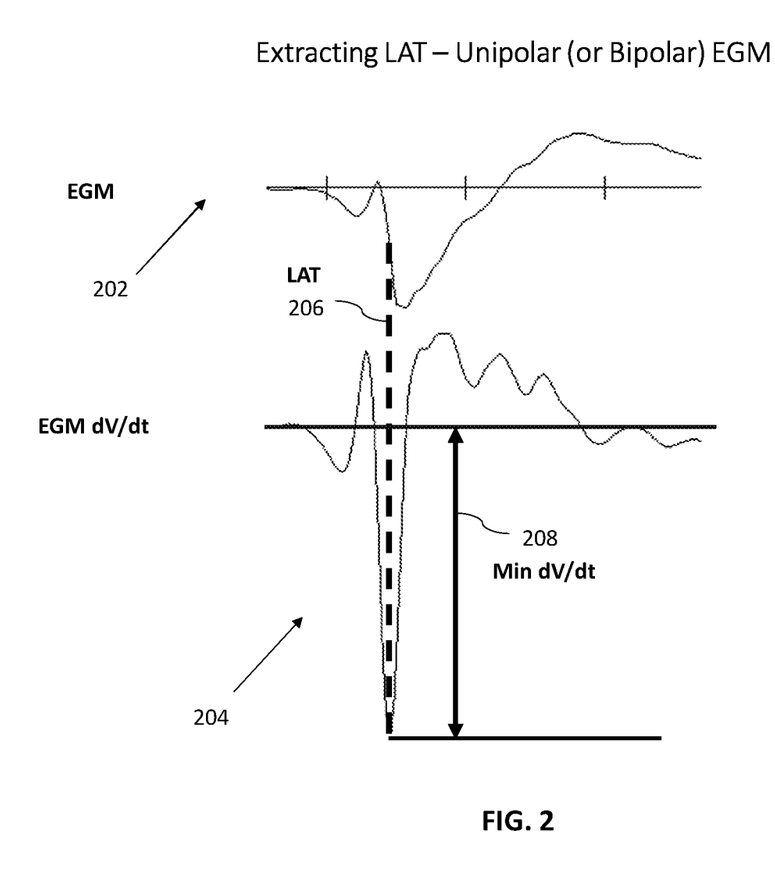
FIG. 2 shows an example of a unipolar EGM and its first derivative with respect to time measured, in accordance with one embodiment of the invention.

FIG. 2 illustrates an example of a unipolar EGM 202 recorded by the system 100 of FIG. 1 and its calculated first derivative with respect to time (EGM dV/dt). Said calculated first derivative is generally indicated by reference numeral 204. The time at which the first derivative of the EGM signal reaches its minimum value 208 is determined as a local activation time (LAT) 206.

Figure 3A:
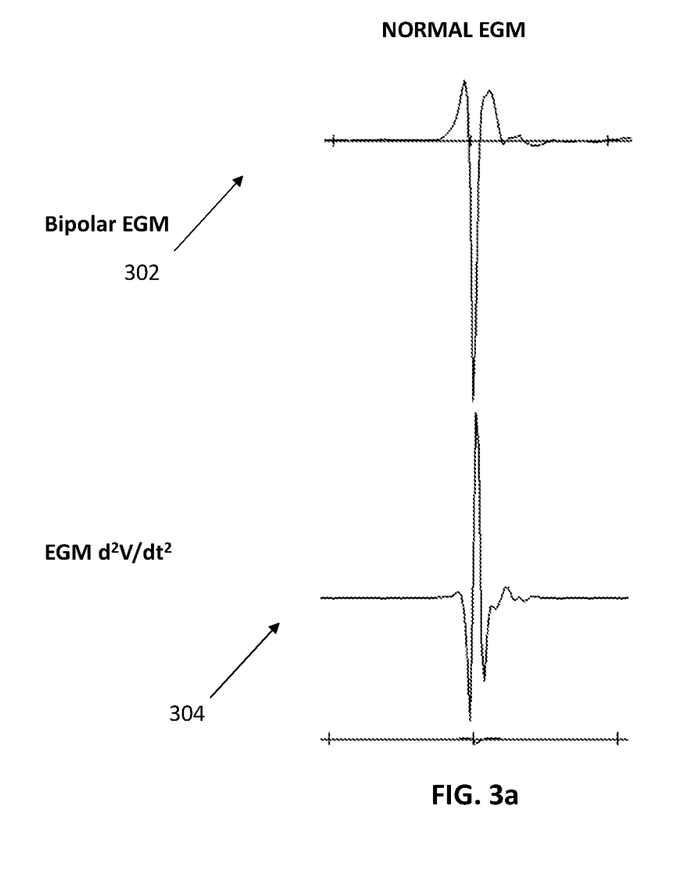
FIGS. 3a and 3b show examples of a normal and an abnormal (highly fractionated) bipolar EGMs and their second derivatives with respect to time, $d^2V/dt^2$, in accordance with one embodiment of the invention.
Figure 3B:
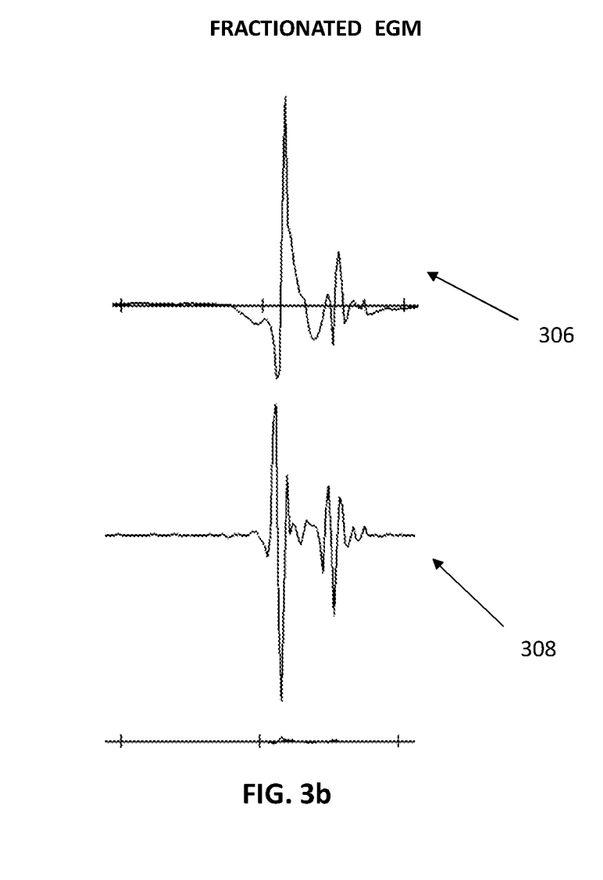

FIG. 3a illustrates a bipolar EGM in normal heart tissue indicated generally by reference numeral 302 for the bipolar case and its second derivative with respect to time indicated generally by reference numeral 304. The bipolar EGM 302 is considered normal in the sense that there is no fractionation occurring in the signal and is indicative of normal cardiac tissue. FIG. 3b shows a fractionated bipolar EGM indicated generally by reference numeral 306 and its second derivative with respect to time indicated generally by reference numeral 308. The EGM indicated by reference numeral 306 is indicative of diseased or abnormal cardiac tissue as it exhibits a high degree of fractionation. Thus, it will be appreciated that a metric that indicative of the degree of fractionation in an EGM may be used to characterize a condition of cardiac tissue as normal or abnormal. Embodiments of the present invention, advantageously, disclose techniques to compute a metric that is indicative of the degree of fractionation in an EGM, as will be explained.

Figure 4:
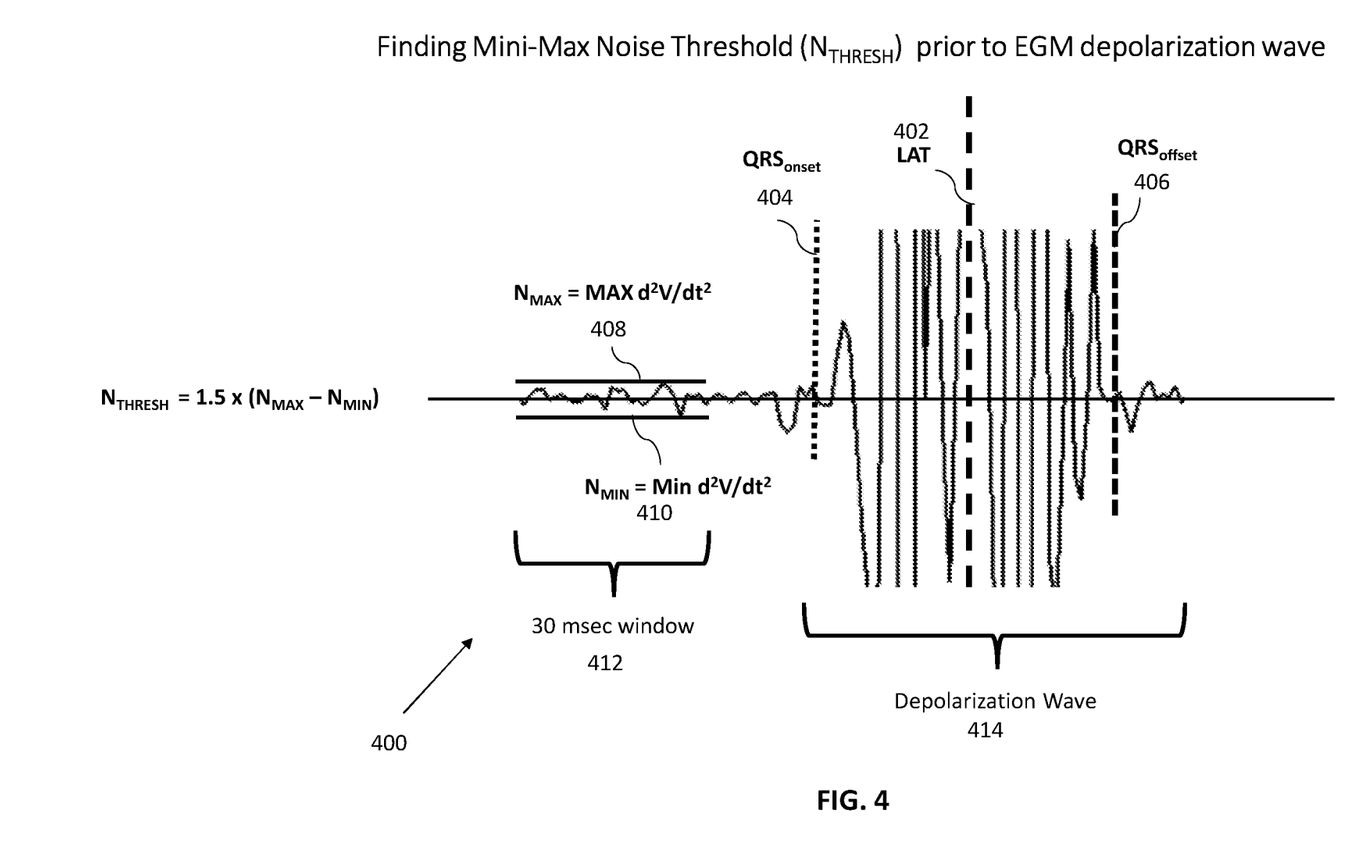
FIG. 4 shows an example of a second derivative with respect to time of an EGM in an expanded scale, a depolarization wave, $QRS_{onset}$, and $QRS_{end}$ (QRS offset), and the technique of setting a noise threshold, in accordance with one embodiment of the invention is illustrated.

FIG. 4 illustrates an amplified second derivative of an EGM signal wave and illustrates some aspects of a method performed in accordance with one embodiment of the invention to quantify the degree of fractionation in an EGM. The method is performed by the system 100 described above and begins by determining a noise level for each EGM in a low amplitude portion 412 of the EGM prior to QRS onset. As will be seen, the EGM comprises a high amplitude portion which corresponds to the depolarization wave indicated by reference numeral 414. The depolarization wave 414 begins at the point numeral 404 which corresponds to the QRS onset and ends at the point numeral 406 which corresponds to an end or termination of the QRS complex. For purposes of the techniques disclosed herein, the point indicated by reference numeral forward to corresponds to the Local Activation Time (LAT) which is generally measured as that point within the QRS complex that is indicative of a maximum deviation in the EGM signal. The noise level is determined in that portion of the EGM signal within a 30-millisecond window 412 preceding the QRS wave 414. The noise level is computed as the range between a minimum 410 and a maximum 408 (mini-max) value of the second derivative of the signal in the 30-millisecond window 412 preceding $QRS_{onset}$ 414. In some embodiments, the 30-millisecond window 412 can be searched after $QRS_{end}$ 414. The 30-millisecond window 412 depicts a time when there is minimum cardiac activity in the heart muscles.

The difference of the maximum noise level and the minimum noise level is multiplied by a safety factor, e.g. 1.5, to obtain a noise threshold level. This noise threshold level $N_{THRESH}$ may be used to determine a beginning and an end of the QRS wave ($QRS_{onset}$ to $QRS_{end}$) 404 and 406 in the EGM signals. The $QRS_{onset}$ time is determined to be the point at which the amplitude of the second derivative with respect to time of the EGM signal becomes greater than $N_{THRESH}$. The $QRS_{END}$ time is determined to the point at which the amplitude of the second derivative with respect to time of the EGM signal becomes less than $N_{THRESH}$.

Figure 5:
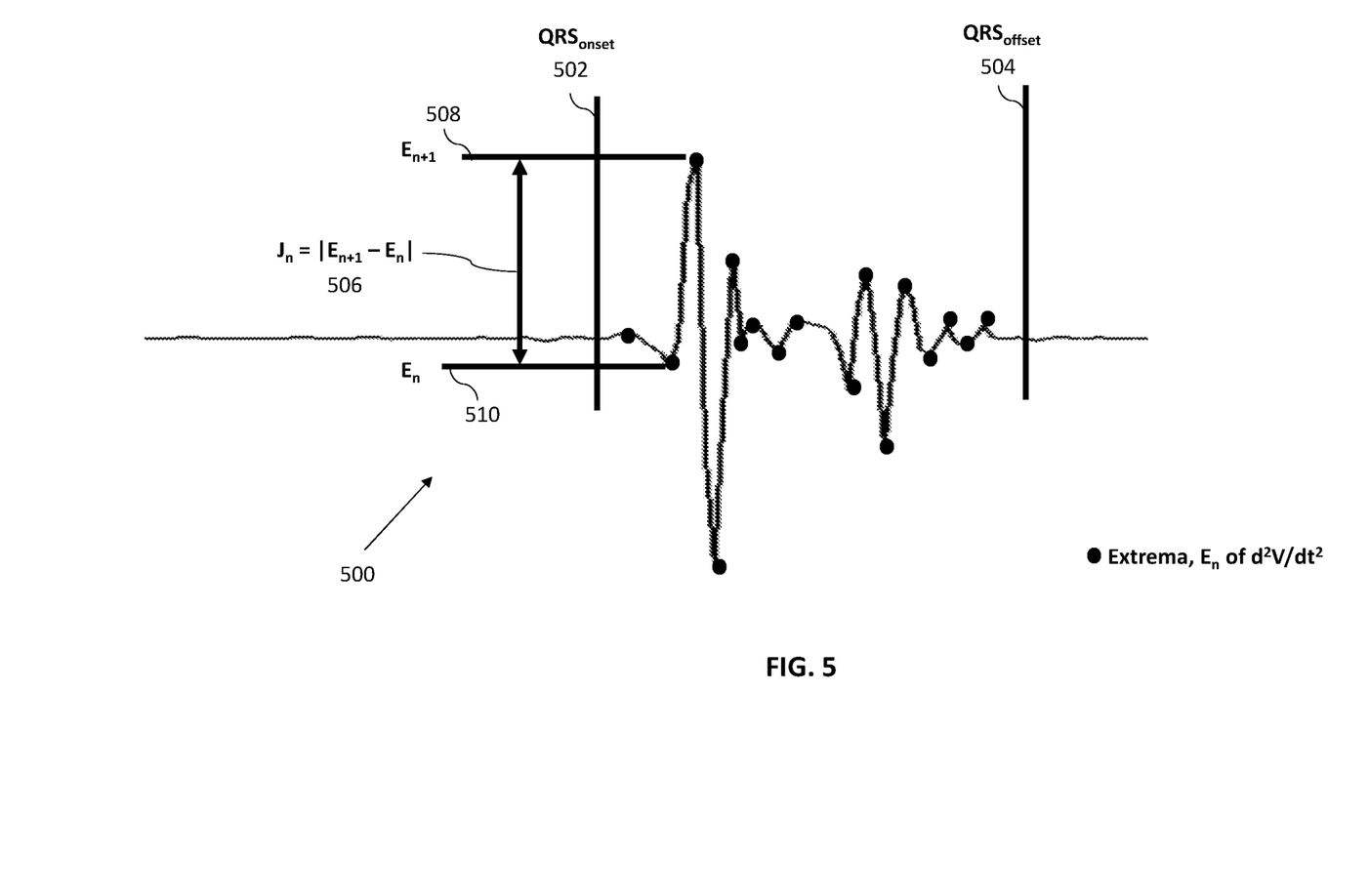
FIG. 5 shows a second derivative with respect to time of an EGM and detection of its extrema (peaks and nadirs of a waveform) and the depiction of excursions (jumps), amplitude differences between adjacent extrema, in accordance with one embodiment of the invention is illustrated.

FIG. 5 illustrates a method for determining extrema (peaks and nadirs, $\{E_n\}$) 510 of the EGM wave's second derivative with respect to time, ($d^2V/dt^2$). These are tabulated for both the 30-millisecond window 412 as shown in FIG. 4 preceding the QRS wave and for the QRS interval 414 as shown in FIG. 4. An EGM specific noise threshold is defined as 1.5 times the largest excursion in the 30-millisecond mini-max window 412 as shown in FIG. 4. Fractionation is quantified as the number of excursions in the QRS interval 414 as shown in FIG. 4 greater or equal to the threshold. Once the $QRS_{onset}$ 502 and $QRS_{end}$ 504 times have been demarcated, a value of each excursion in the QRS, for example $J_n$ depicted by reference numeral 506 in the bi-polar signal, is determined and compared with the threshold. $J_n$ is determined to be the difference between adjacent extrema in the EGM signal corresponding to points $E_{n+1}$ 508 and $E_n$ 510 and is compared with the threshold. In case, the value of $J_n$ is greater than the threshold it is considered as a significant excursion and the number of excursions is increased by 1. The total number of significant excursions in the QRS is called the fractionation number for the EGM.

Figure 6A:
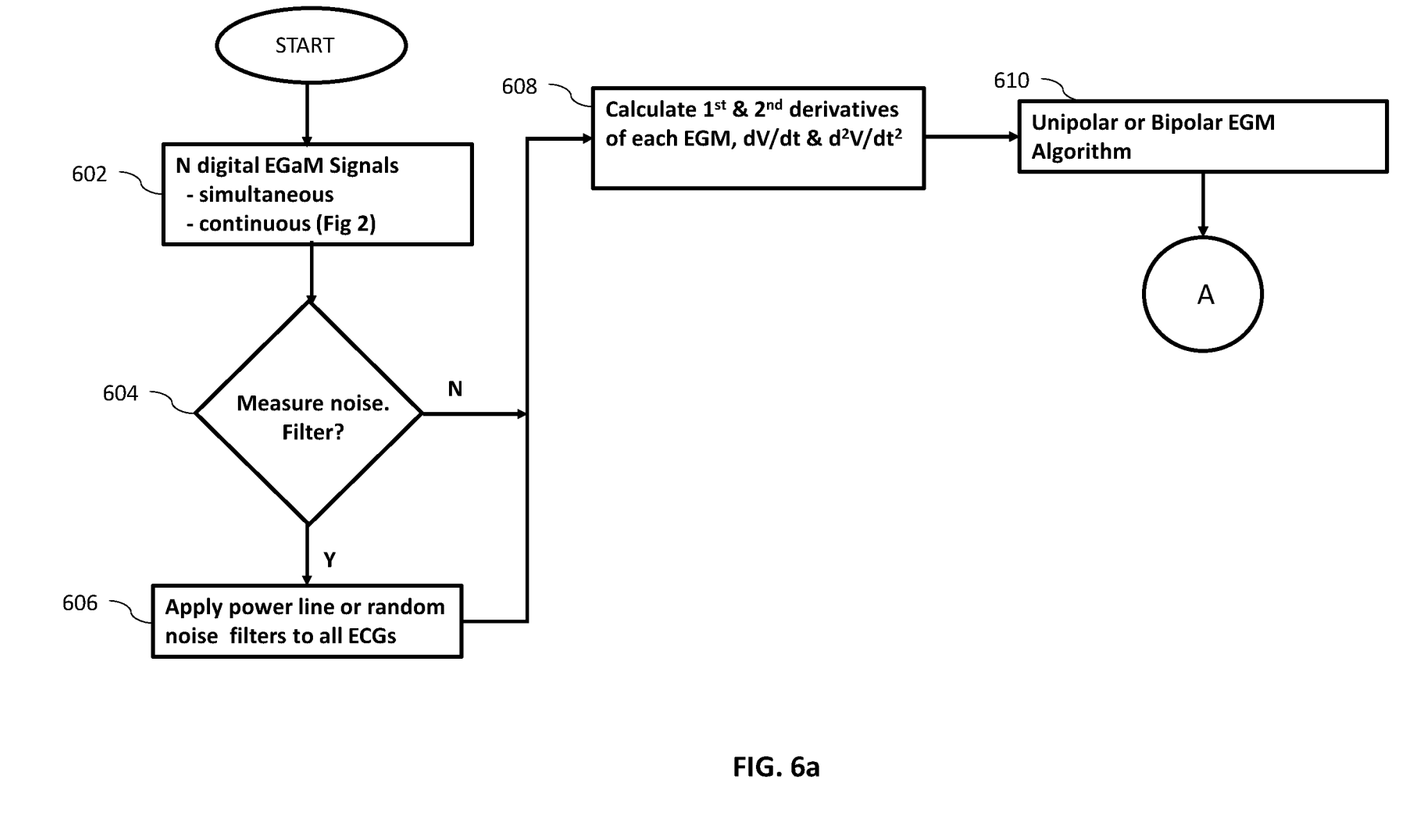
FIGS. 6a and 6b show flowcharts of an algorithm for measuring EGM fractionation, in accordance with one embodiment of the invention.
Figure 6B:
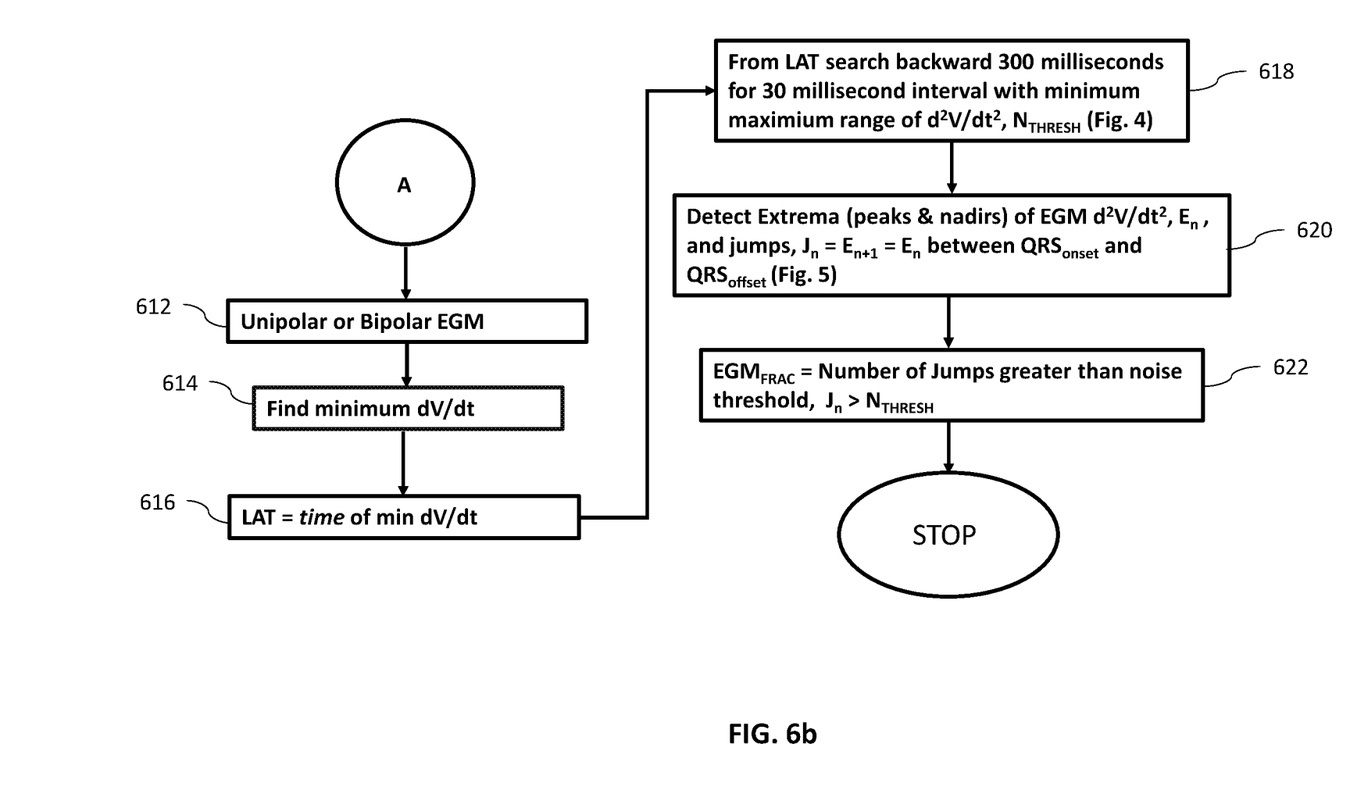

FIG. 6a and FIG. 6b illustrates the processing performed by the computing device 120 of FIG. 1. The computing device 120 may perform removal of noise from N digital EGM signals received from the electrodes 112 of FIG. 1 in block 602.

At block 604, a noise level in the signals is measured and compared with a threshold, and if the noise level is above the threshold then noise reduction is performed at block 606.

If the noise level is below the threshold or once EGM signals with appropriate noise levels are obtained, processing may be transitioned to block 608 which may include calculation of a first derivative with respect to time of N signals and a second derivative with respect to time of the N EGM signals received. The first derivative with respect to time of the signals may be computed according to the following equation:

Equation for calculating the first derivative with respect to time of the EGM: Least mean squared error (LMSE) parabolic fit of data:

$$\frac{d}{dt} jEGM_k = A \sum_{i=1}^{n} i(jEGM_{k+i} - jEGM_{k-i})$$

where j EGM is the $j^{th}$ EGM, k is the sample time, and A is a dependent on n.

Similarly, the second derivative with respect to time of the EGM is calculated as:

$$\frac{d^2}{dt^2} jEGM_k = B \sum_{i=1}^{n} (jECG_{i+k} + jECG_{i-k}) + C \sum_{i=1}^{n} i^2 (jECG_{i+k} + jECG_{i-k})$$

Where $_jECG_k$ is the $j^{th}$ EGM, k is the sample time and B and C are constants dependent on n.

At block 610 detection of a depolarization wave is performed and determination of a window in the EGM signal around the time when the absolute value of dv/dt is at a maximum.

Referring to FIG. 6b, at block 612 a determination is made if the EGM signal is a unipolar or a bipolar signal. At block 614 a minimum value of a first derivative with respect to time of the EGM signal is determined. The time at which the first derivative is minimum is determined to be a local activation time (LAT) in block 616.

At block 618 a search is performed for a 30-millisecond window to determine a min-max range of second derivative with respect to time of the EGM signal by searching 300 milliseconds backwards from the LAT time as described in FIG. 4.

Once the 30-millisecond window 412 as shown in FIG. 4 is determined, detection of extrema (peaks and nadirs) in the QRS window 414 as shown in FIG. 4 of the second derivatives with respect to time of the EGM signals is performed in block 620 as described in FIG. 5. And one embodiment extrema in the window may be determined and the maximum excursion in the window determined. The 30-millisecond window having the minimum maximum excursion sets the noise threshold for the EGM.

At block 622, an EGM fractionation value is determined the number excursions greater than noise threshold $N_{THRESH}$ as described in FIG. 4 and FIG. 5.

Thus, the value of EGM fractionation determined gives an accurate measure of abnormality in the cardiac muscle tissue.

Figure 7:
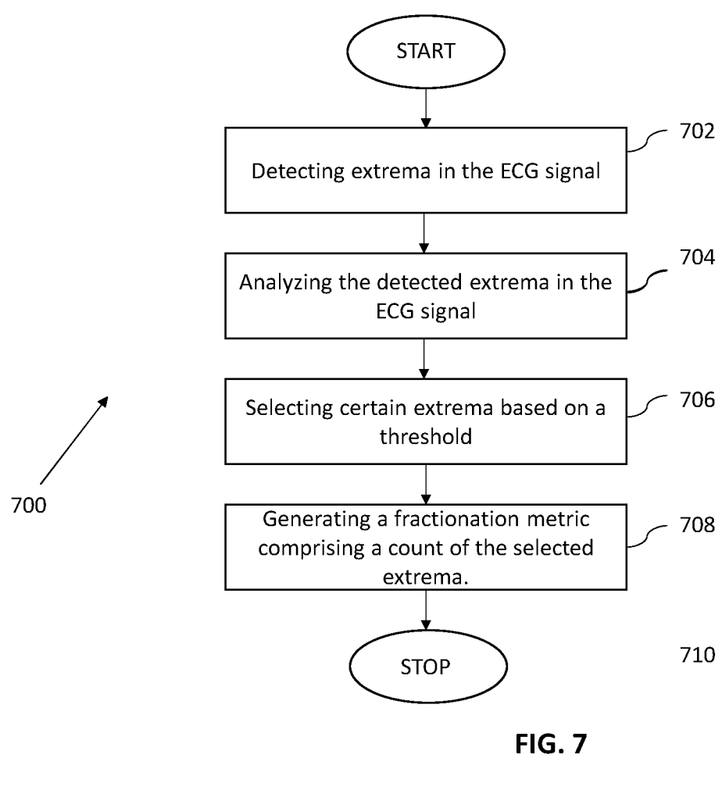
FIG. 7 shows a flowchart depicting a method for quantifying a metric indicative of a condition of cardiac tissue in an electrogram, in accordance with one embodiment of the invention.

FIG. 7 shows a flowchart depicting a method for quantifying a metric indicative of a condition of cardiac tissue in an electrogram, in accordance with one embodiment of the invention. At block 702, extrema in the ECG signal is detected as described in FIG. 5. At block 704 the detected extrema are analyzed as described in FIG. 5. At block 706, extrema which are analyzed in block 704 are selected based on a threshold value of noise as described in FIGS. 4 and 5. At block 708 a fractionation metric is generated which comprises a count of the selected extrema in block 706.

Figure 8:
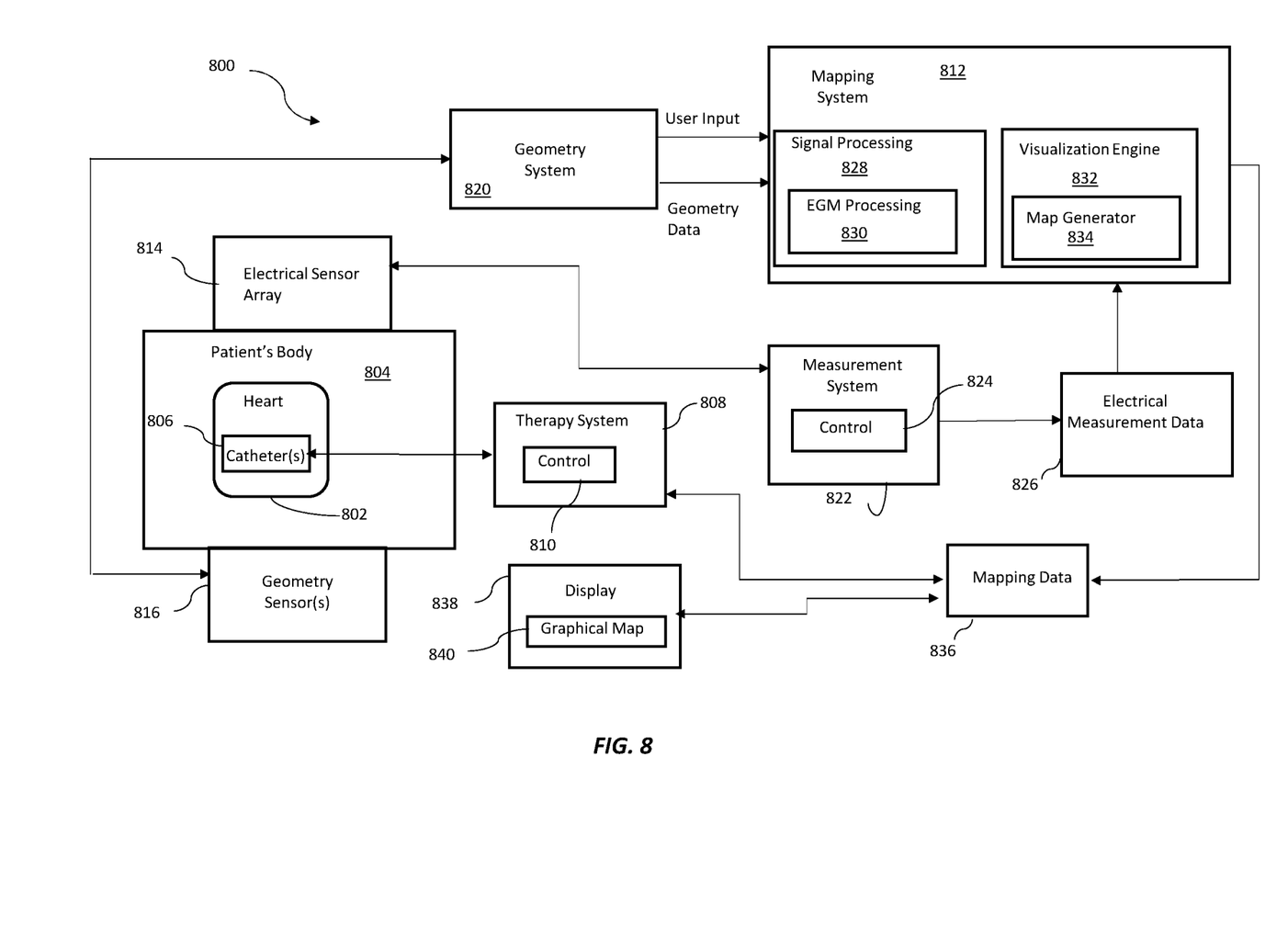
FIG. 8 of the drawings shows an exemplary diagnostic/treatment system, in accordance with one embodiment of the invention.

FIG. 8 of the drawings shows an exemplary diagnostic/treatment system 800, in accordance with one embodiment of the invention. The system 800 is capable of assessing the condition of the heart 802 in real-time as part of a treatment or diagnostic procedure. For this purpose, the system 800 includes one or more catheters that can be inserted into a patient's body 804 thereby to contact the patient's heart 802—more specifically the endocardium or the epicardium. One of ordinary skill in the art would understand and appreciate that various types and configurations of catheters 806 may be utilized, depending on the type of treatment and procedure.

In some cases, the therapy system 806 may include one or more electrodes located at the tip of an ablation catheter which in use is configured to ablate tissue in response to electrical signals (for example radiofrequency energy) supplied by a therapy system 808. In other cases, the therapy delivery device 806 may include one or more electrodes located at the tip of a pacing catheter to deliver electrical stimulation for pacing the heart in response The therapy system 808 may be located external to the patient's body 804 and may be configured to control the type of therapy that is delivered by the device 806. For example, the therapy system 808 may include control circuitry 810 configured to deliver electrical signals by a conductive link electrically connected between the device (electrodes) 806 and the therapy system 808. The control circuitry 810 may provide control parameters for the signals supplied to the device 806 (these may include current, voltage, etc.) For delivering therapy (example ablation) via the electrode(s) 804 to one or more sites within the heart 802, the control circuitry 810 may set therapy parameters and apply stimulation based on automatic, manual (user input) or a combination of automatic and manual mechanisms. In some embodiments, one or more sensors (not shown) may be configured to communicate since the information back to the therapy system 808. The position of the catheter 806 within the heart 802 may be determined and tracked by a mapping system 802. Location of the device 806 and in the therapy parameters may be combined to provide corresponding therapy parameters data.

In some embodiments, prior to providing therapy by the therapy system 808 and other system or subsystem may be utilized to acquire electrophysiological data for the patient. For this purpose, a sensor array 814 including one or more electrodes may be utilized for recording patient activity. In some cases, the sensor array 814 may include an arrangement of body surface sensors distributed over a portion of the patient's torso for measuring electrical activity associated with the patient's heart. The catheter 806 may include one or more electrodes that can be utilized in conjunction with the sensor array 814 for mapping electrical activity of the endocardial surface such as the wall of the heart chamber. Additionally, such electrodes may be used to obtain location or positional information of the catheter 806 within the heart which can advantageously be used to register electrical information of the heart in an image or map is generated by the system 800. In some embodiments, to facilitate the tracking of the catheter 806 positional within the heart, geometry sensors 816 may be positioned around the patient's body and configured to sense the position of the catheter 806 within the heart. For example, in some embodiments, the catheter 806 may be comprise with a magnetic element that can be sensed by the geometry sensors 816 to the to derive catheter positional data that is transmitted to a geometry system 820. The geometry system 820 may be configured to generate geometry data which is then input into the mapping systems 812.

In one embodiment, the sensor array 814 may be configured to provide the sensed electrical information to a corresponding measurement system 822. The measurement system 822 may include control circuitry 824 and signal processing circuitry (not shown) for generating electrical measurement data 826 that describes electrical activity detected by sensors in the sensor array 814. The electrical measurement data 826 may comprise analog and/or digital information. In some embodiments, the control circuitry 824 may be configured to control a data acquisition process for measuring electrical activity of the heart and generating the electrical measurement data 826. The electrical measurement data 826 may be acquired concurrently with the therapy delivered by the therapy system 808.

The mapping system 812 may be configured to combine the electrical measurement data 826 with geometry data generated by the geometry system 820 by applying appropriate processing computations. For example, the mapping system 812 may include a single processing module 828 configured to process the signals generated by the geometry system 820 and measurements system 822. For example, the signal processing module 828 may include an EGM processing module 830 configured to process EGM signals associated with the heart in accordance with the techniques described above including calculating fractionation. A visualize relation engine 832 of the mapping systems and 812 may be provisioned with a mapped generator function 834 configured to render various metrics associated with the heart in visual form. For this purpose, the visualization engine 832 outputs mapping data 836 that can be rendered on a display 838 as a graphical map 840 showing various metrics associated with the heart.

By way of example, the geometry data output but the geometry system 820 may comprise a graphical representation of the patient's torso in the form of image data acquired for the patient. In one embodiment, the geometry system 820 may process the image data to extract and segment anatomical features of the heart. Additionally, positional information for the sensors within the electrical sensor array 814 may be included in the geometry data. The geometry data may be converted into a two-dimensional or three-dimensional graphical representation that includes regions of interest within the patient's heart by the mapping systems 812.

In other embodiments, the geometry data may include a mathematical model of the patient's heart instructed based on image data for the patient. Anatomical or other landmarks, including locations for the electrodes within the sensor array 814 may be identified in the geometry data to facilitate registration of the electrical measurement data 826. Identification of said landmarks may be performed manually based on the user input, or automatically by means of image processing techniques.

The mapped generator 834 may be configured to generate activation maps for the patient's heart, showing various metrics such as electrical activation times, and indications for QRS onset, the DV/DT, fractionation, etc.

In some embodiments, the system 100 acquiring cardiac signals described above may be embedded within the system 800.

In view of the foregoing structural and functional description, those skilled in the art will appreciate that portions of the invention may be embodied as a method, data processing system, or computer program product. Accordingly, these portions of the present invention may take the form of an entirely hardware embodiment, an entirely software embodiment, or an embodiment combining software and hardware, such as shown and described with respect to the computer system of FIG. 9.

Figure 9:
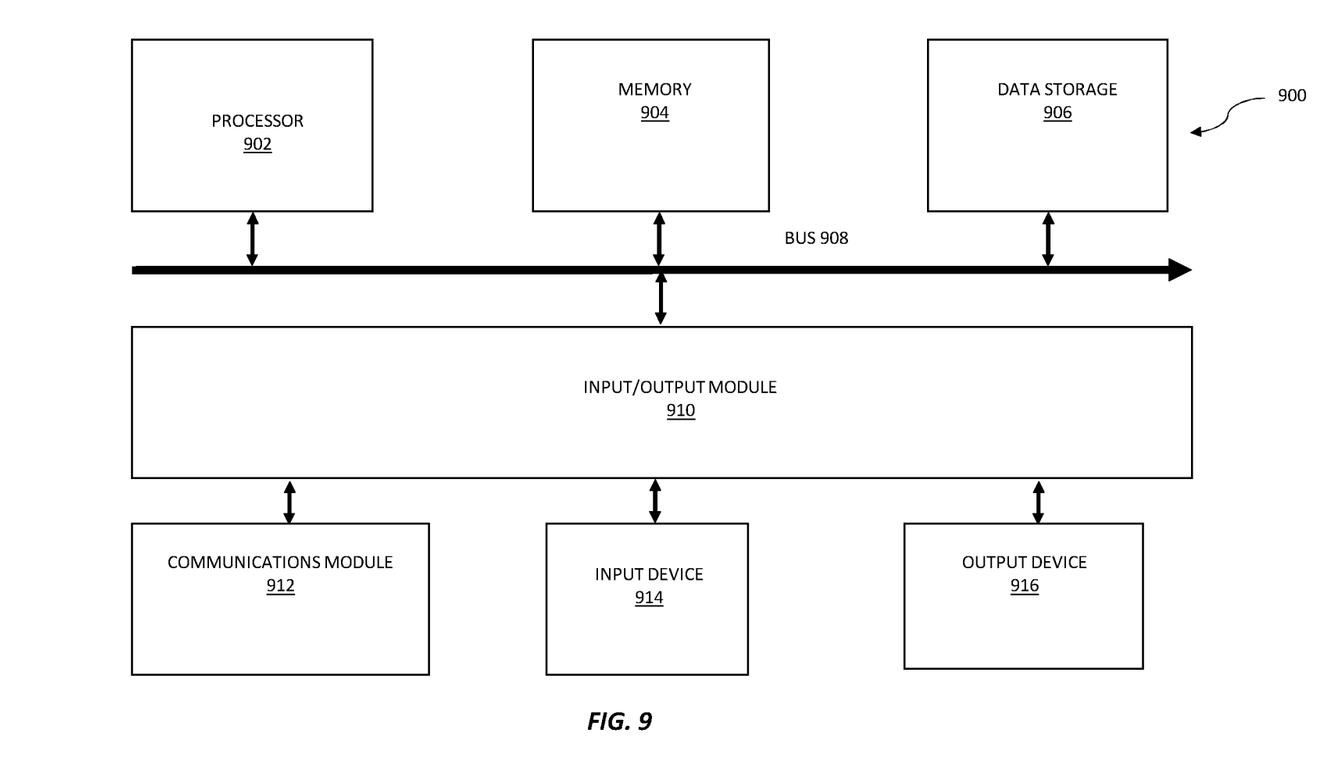
FIG. 9 shows a high-level block diagram of hardware that may be used to practice aspects of the present invention.

FIG. 9 is a block diagram illustrating exemplary hardware for executing some of the techniques disclosed herein, in accordance with one embodiment of the invention. In certain aspects, the computer system 900 may be implemented using hardware or a combination of software and hardware, either in a dedicated server or integrated into another entity or distributed across multiple entities.

Computer system 900 (e.g., client or server) includes a bus 908 or other communication mechanism for communicating information, and a processor 902 coupled with bus 908 for processing information. According to one aspect, the computer system 900 may be implemented as one or more special-purpose computing devices. The special-purpose computing device may be hard-wired to perform the disclosed techniques, or may include digital electronic devices such as one or more application-specific integrated circuits (ASICs) or field programmable gate arrays (FPGAs) that are persistently programmed to perform the techniques, or may include one or more general purpose hardware processors programmed to perform the techniques pursuant to program instructions in firmware, memory, other storage, or a combination. Such special-purpose computing devices may also combine custom hard-wired logic, ASICs, or FPGAs with custom programming to accomplish the techniques. The special-purpose computing devices may be desktop computer systems, portable computer systems, handheld devices, networking devices or any other device that incorporates hard-wired and/or program logic to implement the techniques. By way of example, the computer system 900 may be implemented with one or more processors 902. Processor 902 may be a general-purpose microprocessor, a microcontroller, a Digital Signal Processor (DSP), an ASIC, a FPGA, a Programmable Logic Device (PLD), a controller, a state machine, gated logic, discrete hardware components, or any other suitable entity that can perform calculations or other manipulations of information.

Computer system 900 can include, in addition to hardware, code that creates an execution environment for the computer program in question, e.g., code that constitutes processor firmware, a protocol stack, a database management system, an operating system, or a combination of one or more of them stored in an included memory 904 such as a Random Access Memory (RAM), a flash memory, a Read Only Memory (ROM), a Programmable Read-Only Memory (PROM), an Erasable PROM (EPROM), registers, a hard disk, a removable disk, a CD-ROM, a DVD, or any other suitable storage device, coupled to bus 908 for storing information and instructions to be executed by processor 902. The processor 902 and the memory 904 can be supplemented by, or incorporated in, special purpose logic circuitry. Expansion memory may also be provided and connected to computer system 900 through input/output module 910, which may include, for example, a SIMM (Single in Line Memory Module) card interface. Such expansion memory may provide extra storage space for computer system 900 or may also store applications or other information for computer system 900. Specifically, expansion memory may include instructions to carry out or supplement the processes described above and may include secure information also Thus, for example, expansion memory may be provided as a security module for computer system 900 and may be programmed with instructions that permit secure use of computer system 900. In addition, secure applications may be provided via the SIMM cards, along with additional information, such as placing identifying information on the SIMM card in a non-hackable manner.

The instructions may be stored in the memory 904 and implemented in one or more computer program products, i.e., one or more modules of computer program instructions encoded on a computer readable medium for execution by, or to control the operation of, the computer system 900, and according to any method well known to those of skill in the art, including, but not limited to, computer languages such as data-oriented languages (e.g., SQL, dBase), system languages (e g., C, Objective-C, C++, Assembly), architectural languages (e.g., Java, NET), and application languages (e.g., PHP, Ruby, Perl, Python). Instructions may also be implemented in computer languages such as array languages, aspect-oriented languages, assembly languages, authoring languages, command line interface languages, compiled languages, concurrent languages, curly-bracket languages, dataflow languages, data-structured languages, declarative languages, esoteric languages, extension languages, fourth-generation languages, functional languages, interactive mode languages, interpreted languages, iterative languages, list-based languages, little languages, logic-based languages, machine languages, macro languages, metaprogramming languages, multiparadigm languages, numerical analysis, non-English-based languages, object-oriented class-based languages, object-oriented prototype-based languages, off-side rule languages, procedural languages, reflective languages, rule-based languages, scripting languages, stack-based languages, synchronous languages, syntax handling languages, visual languages, embeddable languages, and xml-based languages Memory 904 may also be used for storing temporary variable or other intermediate information during execution of instructions to be executed by processor 902.

A computer program as discussed herein does not necessarily correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, subprograms, or portions of code). A computer program can be deployed to be executed on one computer or on multiple computers that are located at one site or distributed across multiple sites and interconnected by a communication network. The processes and logic flows described in this specification can be performed by one or more programmable processors executing one or more computer programs to perform functions by operating on input data and generating output.

Computer system 970 further includes a data storage device 906 such as a magnetic disk or optical disk, coupled to bus 908 for storing information and instructions. Computer system 900 may be coupled via input/output module 910 to various devices. The input/output module 910 can be any input/output module Example input/output modules 910 include data ports such as USB ports. In addition, input/output module 910 may be provided in communication with processor 902, so as to enable near area communication of computer system 900 with other devices. The input/output module 910 may provide, for example, for wired communication in some implementations, or for wireless communication in other implementations, and multiple interfaces may also be used. The input/output module 910 is configured to connect to a communications module 912. Example communications modules 912 include networking interface cards, such as Ethernet cards and modems.

The components of the system can be interconnected by any form or medium of digital data communication, e.g., a communication network. The communication network can include, for example, any one or more of a PAN, a LAN, a CAN, a MAN, a WAN, a BBN, the Internet, and the like. Further, the communication network can include, but is not limited to, for example, any one or more of the following network topologies, including a bus network, a star network, a ring network, a mesh network, a star-bus network, tree or hierarchical network, or the like.

For example, in certain aspects, communications module 912 can provide a two-way data communication coupling to a network link that is connected to a local network. Wireless links and wireless communication may also be implemented. Wireless communication may be provided under various modes or protocols, such as GSM (Global System for Mobile Communications), Short Message Service (SMS), Enhanced Messaging Service (EMS), or Multimedia Messaging Service (MMS) messaging, CDMA (Code Division Multiple Access), Time division multiple access (TDMA), Personal Digital Cellular (PDC), Wideband CDMA, General Packet Radio Service (GPRS), or LTE (Long-Term Evolution), among others. Such communication may occur, for example, through a radio-frequency transceiver. In addition, short-range communication may occur, such as using a BLUETOOTH, WI-FI, or other such transceiver.

In any such implementation, communications module 912 sends and receives electrical, electromagnetic or optical signals that carry digital data streams representing various types of information. The network link typically provides data communication through one or more networks to other data devices. For example, the network link of the communications module 912 may provide a connection through local network to a host computer or to data equipment operated by an Internet Service Provider (ISP). The ISP in turn provides data communication services through the world-wide packet data communication network now commonly referred to as the Internet. The local network and Internet both use electrical, electromagnetic or optical signals that carry digital data streams. The signals through the various networks and the signals on the network link and through communications module 912, which carry the digital data to and from computer system 900, are example forms of transmission media.

Computer system 900 can send messages and receive data, including program code, through the network(s), the network link and communications module 912. In the Internet example, a server might transmit a requested code for an application program through Internet, the ISP, the local network and communications module 910. The received code may be executed by processor 902 as it is received, and/or stored in data storage 906 for later execution.

In certain aspects, the input/output module 910 is configured to connect to a plurality of devices, such as an input device 912 (e.g., input device 914) and/or an output device 914 (e.g., output device 914). Example input devices 912 include a stylus, a finger, a keyboard and a pointing device, e.g., a mouse or a trackball, by which a user can provide input to the computer system 900. Other kinds of input devices 912 can be used to provide for interaction with a user as well, such as a tactile input device, visual input device, audio input device, or brain-computer interface device. For example, feedback provided to the user can be any form of sensory feedback, e.g., visual feedback, auditory feedback, or tactile feedback; and input from the user can be received in any form, including acoustic, speech, tactile, or brain wave input. Example output devices 914 include display devices, such as a LED (light emitting diode), CRT (cathode ray tube), LCD (liquid crystal display) screen, a TFT LCD (Thin-Film-Transistor Liquid Crystal Display) or an OLED (Organic Light Emitting Diode) display, for displaying information to the user. The output device 914 may comprise appropriate circuitry for driving the output device 914 to present graphical and other information to a user.

According to one aspect of the present disclosure, the techniques disclosed herein may be implemented on the computer system 900 in response to processor 902 executing one or more sequences of one or more instructions contained in memory 904. Such instructions may be read into memory 904 from another machine-readable medium, such as data storage device 906. Execution of the sequences of instructions contained in main memory 904 causes processor 902 to perform the process steps described herein. One or more processors in a multi-processing arrangement may also be employed to execute the sequences of instructions contained in memory 904. In alternative aspects, hard-wired circuitry may be used in place of or in combination with software instructions to implement various aspects of the present disclosure. Thus, aspects of the present disclosure are not limited to any specific combination of hardware circuitry and software.

Various aspects of the subject matter described in this specification can be implemented in a computing system that includes a back end component, e.g., a data server, or that includes a middleware component, e.g., an application server, or that includes a front end component, e.g., a client computer having a graphical user interface or a Web browser through which a user can interact with an implementation of the subject matter described in this specification, or any combination of one or more such back end, middleware, or front end components.

Computing system 900 can include clients and servers. A client and server are generally remote from each other and typically interact through a communication network. The relationship of client and server arises by virtue of computer programs running on the respective computers and having a client-server relationship to each other. Computer system 900 can be, for example, and without limitation, a desktop computer, laptop computer, or tablet computer. Computer system 900 can also be embedded in another device, for example, and without limitation, a mobile telephone, a personal digital assistant (PDA), a mobile audio player, a Global Positioning System (GPS) receiver, a video game console, and/or a television set top box.

The term "machine-readable storage medium" or "computer-readable medium" as used herein refers to any medium or media that participates in providing instructions or data to processor 902 for execution. The term "storage medium" as used herein refers to any non-transitory media that store data and/or instructions that cause a machine to operate in a specific fashion. Such a medium may take many forms, including, but not limited to, non-volatile media, volatile media, and transmission media. Non-volatile media include, for example, optical disks, magnetic disks, or flash memory, such as data storage device 906. Volatile media include dynamic memory, such as memory 904. Transmission media include coaxial cables, copper wire, and fiber optics, including the wires that comprise bus 908. Common forms of machine-readable media include, for example, floppy disk, a flexible disk, hard disk, magnetic tape, any other magnetic medium, a CD-ROM, DVD, any other optical medium, punch cards, paper tape, any other physical medium with patterns of holes, a RAM, a PROM, an EPROM, a FLASH EPROM, any other memory chip or cartridge, or any other medium from which a computer can read. The machine-readable storage medium can be a machine-readable storage device, a machine-readable storage substrate, a memory device, a composition of matter affecting a machine-readable propagated signal, or a combination of one or more of them.

As used in this specification of this application, the terms "computer-readable storage medium" and "computer-readable media" are entirely restricted to tangible, physical objects that store information in a form that is readable by a computer. These terms exclude any wireless signals, wired download signals, and any other ephemeral signals. Storage media is distinct from but may be used in conjunction with transmission media. Transmission media participates in transferring information between storage media. For example, transmission media includes coaxial cables, copper wire and fiber optics, including the wires that comprise bus 908. Transmission media can also take the form of acoustic or light waves, such as those generated during radio-wave and infra-red data communications. Furthermore, as used in this specification of this application, the terms "computer", "server", "processor", and "memory" all refer to electronic or other technological devices. These terms exclude people or groups of people. For the purposes of the specification, the terms display or displaying means displaying on an electronic device.

To illustrate the interchangeability of hardware and software, items such as the various illustrative blocks, modules, components, methods, operations, instructions, and algorithms have been described generally in terms of their functionality Whether such functionality is implemented as hardware, software or a combination of hardware and software depends upon the particular application and design constraints imposed on the overall system. Skilled artisans may implement the described functionality in varying ways for each particular application.

As used herein, the phrase "at least one of" preceding a series of items, with the terms "and" or "or" to separate any of the items, modifies the list as a whole, rather than each member of the list (i.e., each item). The phrase "at least one of" does not require selection of at least one item; rather, the phrase allows a meaning that includes at least one of any one of the items, and/or at least one of any combination of the items, and/or at least one of each of the items. By way of example, the phrases "at least one of A, B, and C" or "at least one of A, B, or C" each refer to only A, only B, or only C; any combination of A, B, and C; and/or at least one of each of A, B, and C.

To the extent that the term "include," "have," or the like is used in the description or the claims, such term is intended to be inclusive in a manner similar to the term "comprise" as "comprise" is interpreted when employed as a transitional word in a claim. Phrases such as an aspect, the aspect, another aspect, some aspects, one or more aspects, an implementation, the implementation, another implementation, some implementations, one or more implementations, an embodiment, the embodiment, another embodiment, some embodiments, one or more embodiments, a configuration, the configuration, another configuration, some configurations, one or more configurations, the subject technology, the disclosure, the present disclosure, other variations thereof and alike are for convenience and do not imply that a disclosure relating to such phrase(s) is essential to the subject technology or that such disclosure applies to all configurations of the subject technology. A disclosure relating to such phrase(s) may apply to all configurations, or one or more configurations. A disclosure relating to such phrase (s) may provide one or more examples A phrase such as an aspect or some aspects may refer to one or more aspects and vice versa, and this applies similarly to other foregoing phrases.

A reference to an element in the singular is not intended to mean "one and only one" unless specifically stated, but rather "one or more." The term "some" refers to one or more. Underlined and/or italicized headings and subheadings are used for convenience only, do not limit the subject technology, and are not referred to in connection with the interpretation of the description of the subject technology. Relational terms such as first and second and the like may be used to distinguish one entity or action from another without necessarily requiring or implying any actual such relationship or order between such entities or actions. All structural and functional equivalents to the elements of the various configurations described throughout this disclosure that are known or later come to be known to those of ordinary skill in the art are expressly incorporated herein by reference and intended to be encompassed by the subject technology. Moreover, nothing disclosed herein is intended to be dedicated to the public regardless of whether such disclosure is explicitly recited in the above description. No claim element is to be construed under the provisions of 35 U.S.C. § 112, sixth paragraph, unless the element is expressly recited using the phrase "means for" or, in the case of a method claim, the element is recited using the phrase "step for."

While this specification contains many specifics, these should not be construed as limitations on the scope of what may be claimed, but rather as descriptions of particular implementations of the subject matter. Certain features that are described in this specification in the context of separate embodiments can also be implemented in combination in a single embodiment. Conversely, various features that are described in the context of a single embodiment can also be implemented in multiple embodiments separately or in any suitable sub-combination. Moreover, although features may be described above as acting in certain combinations and even initially claimed as such, one or more features from a claimed combination can in some cases be excised from the combination, and the claimed combination may be directed to a sub-combination or variation of a sub-combination.

The subject matter of this specification has been described in terms of particular aspects, but other aspects can be implemented and are within the scope of the following claims. For example, while operations are depicted in the drawings in a particular order, this should not be understood as requiring that such operations be performed in the particular order shown or in sequential order, or that all illustrated operations be performed, to achieve desirable results. The actions recited in the claims can be performed in a different order and still achieve desirable results. As one example, the processes depicted in the accompanying figures do not necessarily require the particular order shown, or sequential order, to achieve desirable results. In certain circumstances, multitasking and parallel processing may be advantageous. Moreover, the separation of various system components in the aspects described above should not be understood as requiring such separation in all aspects, and it should be understood that the described program components and systems can generally be integrated together in a single software product or packaged into multiple software products.

The title, background, brief description of the drawings, abstract, and drawings are hereby incorporated into the disclosure and are provided as illustrative examples of the disclosure, not as restrictive descriptions. It is submitted with the understanding that they will not be used to limit the scope or meaning of the claims. In addition, in the detailed description, it can be seen that the description provides illustrative examples, and the various features are grouped together in various implementations for the purpose of streamlining the disclosure. The method of disclosure is not to be interpreted as reflecting an intention that the claimed subject matter requires more features than are expressly recited in each claim. Rather, as the claims reflect, inventive subject matter lies in less than all features of a single disclosed configuration or operation. The claims are hereby incorporated into the detailed description, with each claim standing on its own as a separately claimed subject matter.

The claims are not intended to be limited to the aspects described herein but are to be accorded the full scope consistent with the language claims and to encompass all legal equivalents. Notwithstanding, none of the claims are intended to embrace subject matter that fails to satisfy the requirements of the applicable patent law, nor should they be interpreted in such a way.

The invention claimed is:

1. A method for quantifying a metric indicative of a condition of cardiac tissue in an electrogram, comprising:

obtaining, by a processor, a noise threshold in a portion of the electrogram before a depolarization wave, based on a maximum noise level and a minimum noise level of a second derivative of the electrogram;

detecting, by the processor, extrema in the electrogram;

comparing, by the processor, the detected extrema with the obtained noise threshold;

selecting, by the processor, each extrema that crosses the obtained noise threshold;

generating, by the processor, a fractionation metric comprising a count of the selected extrema, wherein said fractionation metric is indicative of the condition of the cardiac tissue as normal or abnormal; and controlling, by the processor, display of said fractionation metric as a graphical map.

2. The method of claim 1, wherein detecting the extrema comprises detecting extrema in a portion of the electrogram corresponding to the depolarization wave.

3. The method of claim 1, wherein analyzing the extrema comprises measuring a magnitude of an excursion in the electrogram between two adjacent extrema.

4. The method of claim 3, wherein selecting certain extrema comprises selecting said two adjacent extrema when the magnitude of the excursion between said extrema is above the noise threshold.

5. The method of claim 1, wherein generating the fractionation metric comprises counting adjacent extrema in the electrogram between points where a QRS complex begins and ends.

6. A system to quantify a metric indicative of a condition of cardiac tissue in an electrogram, comprising:

one or more electrodes to acquire the electrogram; and one or more processors coupled to a memory programmed with executable instructions to:

obtain a noise threshold in a portion of the electrogram before a depolarization wave, based on a maximum noise level and a minimum noise level of a second derivative of the electrogram;

detect an extrema in the electrogram;

compare the detected extrema with the obtained noise threshold;

select each extrema that crosses the obtained noise threshold;

generate a fractionation metric comprising a count of the selected extrema, wherein said fractionation metric is indicative of the condition of the cardiac tissue as normal or abnormal; and control a display screen to display said fractionation metric as a graphical map.

7. The system of claim 6, wherein detection of the extrema comprises detecting extrema in a portion of the electrogram corresponding to the depolarization wave.

8. The system of claim 6, wherein analyzation of the extrema comprises measuring a magnitude of an excursion in the electrogram between two adjacent extrema.

9. The system of claim 8, wherein selecting certain extrema comprises selecting said two adjacent extrema when the magnitude of the excursion between said two adjacent extrema is above the noise threshold.

10. The system of claim 6, wherein generation of the fractionation metric comprises counting adjacent extrema in the electrogram between points where a QRS complex begins and ends.

11. A non-transitory computer readable storage medium, having stored thereon, a set of computer-executable instructions that causes a computer to perform the method comprising:

obtaining a noise threshold in a portion of the electrogram before a depolarization wave, based on a maximum noise level and a minimum noise level of a second derivative of the electrogram;

detecting extrema in the electrogram signal;

comparing the detected extrema with the obtained noise threshold;

selecting each extrema that crosses the obtained noise threshold;

generating a fractionation metric comprising a count of the selected extrema, wherein said fractionation metric is indicative of the condition of the cardiac tissue as normal or abnormal; and controlling display of said fractionation metric as a graphical map.

12. The non-transitory computer readable storage medium of claim 11, wherein detecting the extrema comprises detecting extrema in a portion of the electrogram corresponding to the depolarization wave.

13. The non-transitory computer readable storage medium of claim 11, analyzing the extrema comprises measuring a magnitude of an excursion in the electrogram between two adjacent extrema.

14. The non-transitory computer readable storage medium of claim 13, wherein selecting certain extrema comprises selecting said two adjacent extrema when the magnitude of the excursion between said extrema is above the noise threshold.

15. The method of claim 11, wherein generating the fractionation metric comprises counting adjacent extrema in the electrogram between points where a QRS complex begins and ends.

* * * * *